United States Patent
Hoyns

(12)
(10) Patent No.: US 6,393,312 B1
(45) Date of Patent: May 21, 2002

(54) CONNECTOR FOR COUPLING AN OPTICAL FIBER TISSUE LOCALIZATION DEVICE TO A LIGHT SOURCE

(75) Inventor: Dirk V. Hoyns, Conyers, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/416,930

(22) Filed: Oct. 13, 1999

(51) Int. Cl.[7] .................................................. A61B 5/00
(52) U.S. Cl. ............................ 600/407; 600/478; 606/2
(58) Field of Search ................................. 600/478, 473, 600/476, 344, 407, 342; 606/2, 3–18

(56) References Cited

U.S. PATENT DOCUMENTS

| 4,007,732 A | | 2/1977 | Kvalve et al. | |
|---|---|---|---|---|
| 4,537,193 A | | 8/1985 | Tanner | |
| 4,567,882 A | | 2/1986 | Heller | |
| 5,078,712 A | | 1/1992 | Easley et al. | |
| 5,111,828 A | | 5/1992 | Kornberg et al. | |
| 5,460,182 A | * | 10/1995 | Goodman et al. | 600/473 |
| 5,693,043 A | * | 12/1997 | Kittrell et al. | 606/15 |
| 5,722,426 A | | 3/1998 | Kolff | |
| 5,730,700 A | * | 3/1998 | Walther et al. | 600/104 |
| 5,782,771 A | | 7/1998 | Hussman | |
| 5,902,247 A | * | 5/1999 | Coe et al. | 600/476 |
| 5,983,125 A | * | 11/1999 | Alfano et al. | 600/473 |
| 6,132,425 A | * | 10/2000 | Gough | 606/41 |

FOREIGN PATENT DOCUMENTS

| DE | 92 01 712.6 U | 4/1992 |
|---|---|---|
| GB | 2 210 706 A | 6/1989 |
| WO | WO 94/20013 A1 | 9/1994 |

\* cited by examiner

*Primary Examiner*—Ruth S. Smith
(74) *Attorney, Agent, or Firm*—Kilpatrick Stockton LLP

(57) ABSTRACT

A quick-connect coupling couples an optical fiber tissue localization device to a light source to cause the forward tip of the device to illuminate. The coupling can be quickly, easily, and reliably mounted to the fiber under operating room conditions. The coupling physically isolates the optical fiber from the light source while optically coupling the fiber to the light source, thereby preventing contamination of the light source by a contaminated optical fiber. The coupling is inexpensive to manufacture, such that the coupling is disposable after a single-patient use.

21 Claims, 10 Drawing Sheets

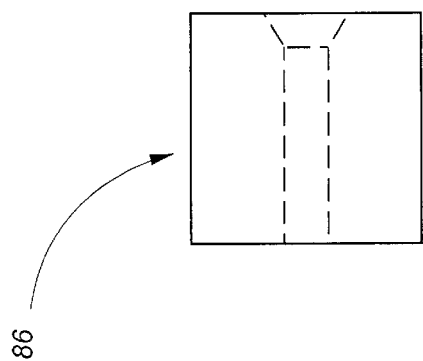
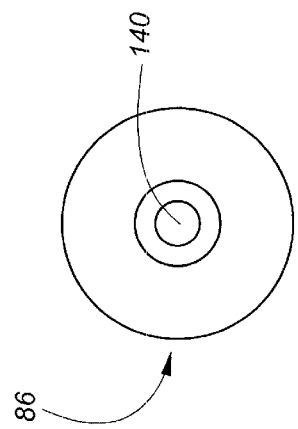
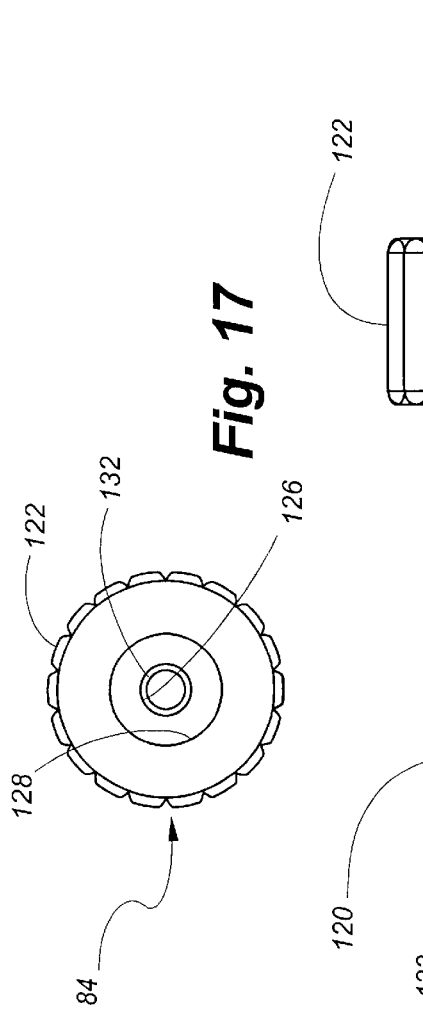
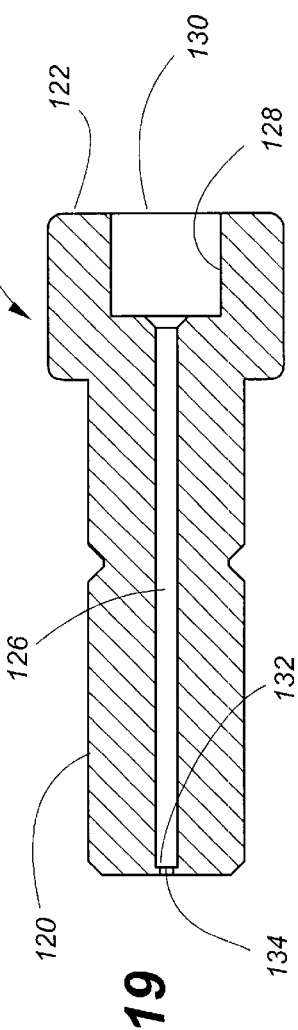

CONNECTOR FOR COUPLING AN OPTICAL FIBER TISSUE LOCALIZATION DEVICE TO A LIGHT SOURCE

TECHNICAL FIELD

The present invention relates generally to guide wires used to localize lesions wherein the guide wires incorporate optical fibers to facilitate visually locating the forward end of the guide wire. More specifically the invention relates to a connector for facilitating coupling the optical fiber of a tissue localization device to a light source.

BACKGROUND OF THE INVENTION

Ultrasound, mammography, magnetic resonance imaging, and other medical imaging modalities are widely used to identify suspicious lesions within the body of a patient. Historically, when a suspicious lesion is located within the body of a patient, a guide wire was inserted by the physician to mark the location of the lesion to enable a surgeon to locate the lesion for removal. The guide wires typically include barbs or hooks at their forward ends to securely anchor the guide within the target tissue.

A problem with such guide wires, however, is that it is sometimes difficult for the surgeon to locate the forward end of the guide wire. While tugging on the guide wire will cause movement at the forward end which the surgeon can visually identify, the tugging action can also dislodge the guide wire from the target tissue. Accordingly, another method of locating the forward end of a guide wire was needed.

To address this problem, the prior art discloses a guide wire fabricated from an optical fiber. Hooks were affixed to the forward end of the optical fiber to anchor the tip of the fiber in the target tissue. The free end of the optical fiber was hooked up to a small laser, and a beam of light was directed through the fiber. A diffuser tip at the forward end of the guide wire created a point of light which could easily be visualized by a surgeon through several centimeters of tissue, thereby facilitating the location of the forward end of the guide wire. U.S. Pat. No. 5,782,771 to Hussman and an article entitled *Optical Breast Lesion Localization Fiber: Preclinical Testing of a New Device* from the September 1996 issue of RADIOLOGY describe the optical fiber localization device in detail.

A problem with respect to prior art optical fiber tissue localization devices concerns the requirement of optically connecting the rearward end of the optical fiber to a light source. A coupling is typically employed to couple an optical fiber to a light source. However, in the case of an optical fiber tissue localization device, the forward end of the device is delivered through a hollow cannula, which must then be withdrawn over the length of the optical fiber and off the rearward end. To permit the cannula to be withdrawn over the rearward end of the optical fiber, the coupling cannot be mounted to the fiber until the forward end of the device is positioned within the patient and the cannula has been withdrawn. Accordingly, the coupling must be quickly, easily, and reliably mounted to the fiber under operating room conditions.

Thus there is a need for a quick-connect coupling for an optical fiber tissue localization device which can be quickly, easily, and reliably mounted to the fiber under operating room conditions.

A further problem concerns the possibility of contaminating the light source and the difficulty of sterilizing the light source. When the cannula is removed from the patient's tissues and withdrawn over the length of the cannula, the entire length of the optical fiber, including its rearward end which couples to the light source, is likely to become contaminated by contact of the contaminated cannula with the optical fiber. Consequently, when the rearward end of the optical fiber is coupled to the light source, the light source may become contaminated. Because it is difficult to sterilize the light source after each procedure, there is a need for an apparatus and method for coupling an optical fiber to a light source which avoids contamination of the light source. There is a further need for an apparatus and method for coupling an optical fiber to a light source wherein the coupling is inexpensive to manufacture, such that the coupling is disposable after a single-patient use.

SUMMARY OF THE INVENTION

Stated generally, the present invention comprises a quick-connect coupling for an optical fiber tissue localization device which can be quickly, easily, and reliably mounted to the fiber under operating room conditions. The coupling physically isolates the optical fiber from the light source while optically coupling the fiber to the light source, thereby preventing contamination of the light source by a contaminated optical fiber. The coupling is inexpensive to manufacture, such that the coupling is disposable after a single-patient use.

Stated somewhat more specifically, an optical fiber has anchor means operatively associated with a forward portion for engaging the tissue of a patient to secure the tip of the optical fiber within the tissue of the patient. A light source is mounted to a mount. A coupling means is provided for coupling the rearward end of the optical fiber to the mount so as to optically couple the light source to the optical fiber.

Thus it is an object of the present invention to provide an improved connector for coupling an optical fiber tissue localization device to a light source.

It is another object of the present invention to provide a quick-connect coupling for an optical fiber tissue localization device which can be quickly, easily, and reliably mounted to the fiber under operating room conditions.

Still another object of the present invention is to provide an apparatus and method for coupling an optical fiber to a light source which avoids contamination of the light source.

It is yet another object of the present invention to provide an apparatus and method for coupling an optical fiber to a light source in accordance with the foregoing objects wherein the coupling is inexpensive to manufacture, such that the coupling is disposable after a single-patient use.

Other objects, features, and advantages of the present invention will become apparent upon reading the following specification, when taken in conjunction with the drawings and the appended claims.

BRIEF DESCRIPTION OF THE DRAWINGS

FIG. 8 shows the insertion of the forward end of the cannula into a suspicious lesion;

FIG. 9 shows the cannula being withdrawn over the optical fiber and the tip of the tissue localization device anchored within the suspicious lesion; and FIG. 10 shows the rearward end of the optical fiber of the tissue localization device hooked up to a light source, with the light source shown schematically.

FIG. 17 is a front view of an adapter which engages the mount of FIG. 12.

FIG. 18 is a side view of the adapter of FIG. 17.

FIG. 19 is a side cutaway view of the adapter of FIG. 17.

FIG. 20 is a side view of an optical fiber retention means in the form of a bushing which fits into the forward end of the adapter of FIG. 17.

FIG. 21 is a front view of the bushing of FIG. 20.

DETAILED DESCRIPTION OF THE DISCLOSED EMBODIMENT

Figure 1:
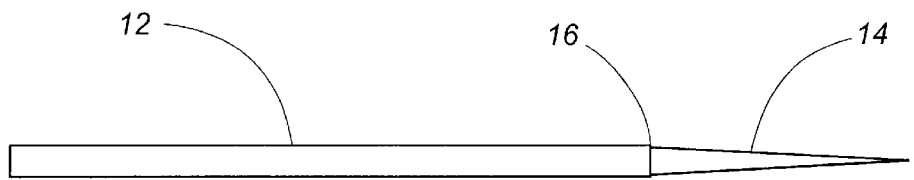
FIG. 1 is a side view of an optical fiber of the tissue localization device of the disclosed embodiment.

Reference is now made to the drawings, in which like numerals indicate like elements throughout the several views. In FIGS. 1–5 an optical fiber tissue localization device 10 includes an optical fiber 12. The optical fiber 12 of the disclosed embodiment is 0.04 inches (1 mm) in diameter and has a nominal length of 1 meter. The optical fiber 12 of the disclosed embodiment is a Mitsubishi ESKA-SK40 fiber optical monofilament, from Mitsubishi International Corporation. The optical fiber 12 has a solid core of acrylic polymer (polymethyl-methacrylate) sheathed with a thin layer of fluorine polymer which has a lower refractive index than the fiber core.

The forward end of the optical fiber is ground into a conical tip 14. The conical tip 14 is approximately 0.4 inches (~10 mm) in length and is tapered at an angle of approximately 2°. To facilitate dispersion of light transmitted down the optical fiber 12, the conical tip 14 has a matte finish on its external surface. A junction 16 indicates the location where the rearward end of the conical tip 14 joins the main body of the optical fiber 12.

Figure 2:
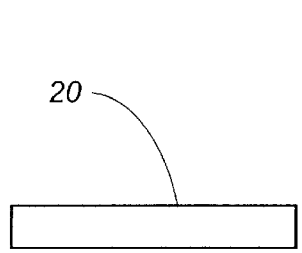
FIG. 2 is a side view of a strain relief tube of the tissue localization device of the disclosed embodiment.
Figure 4:
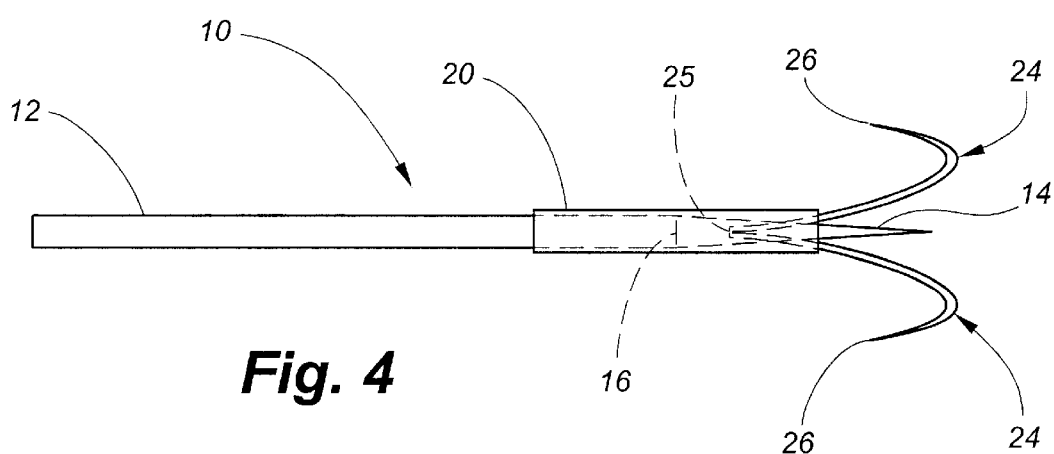
FIG. 4 is a side view of the assembled tissue localization device of the disclosed embodiment.
Figure 5:
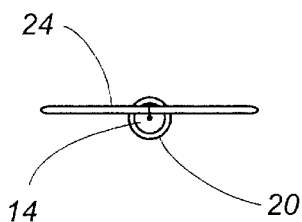
FIG. 5 is a front view of the tissue localization device of FIG. 4.
Figure 6:
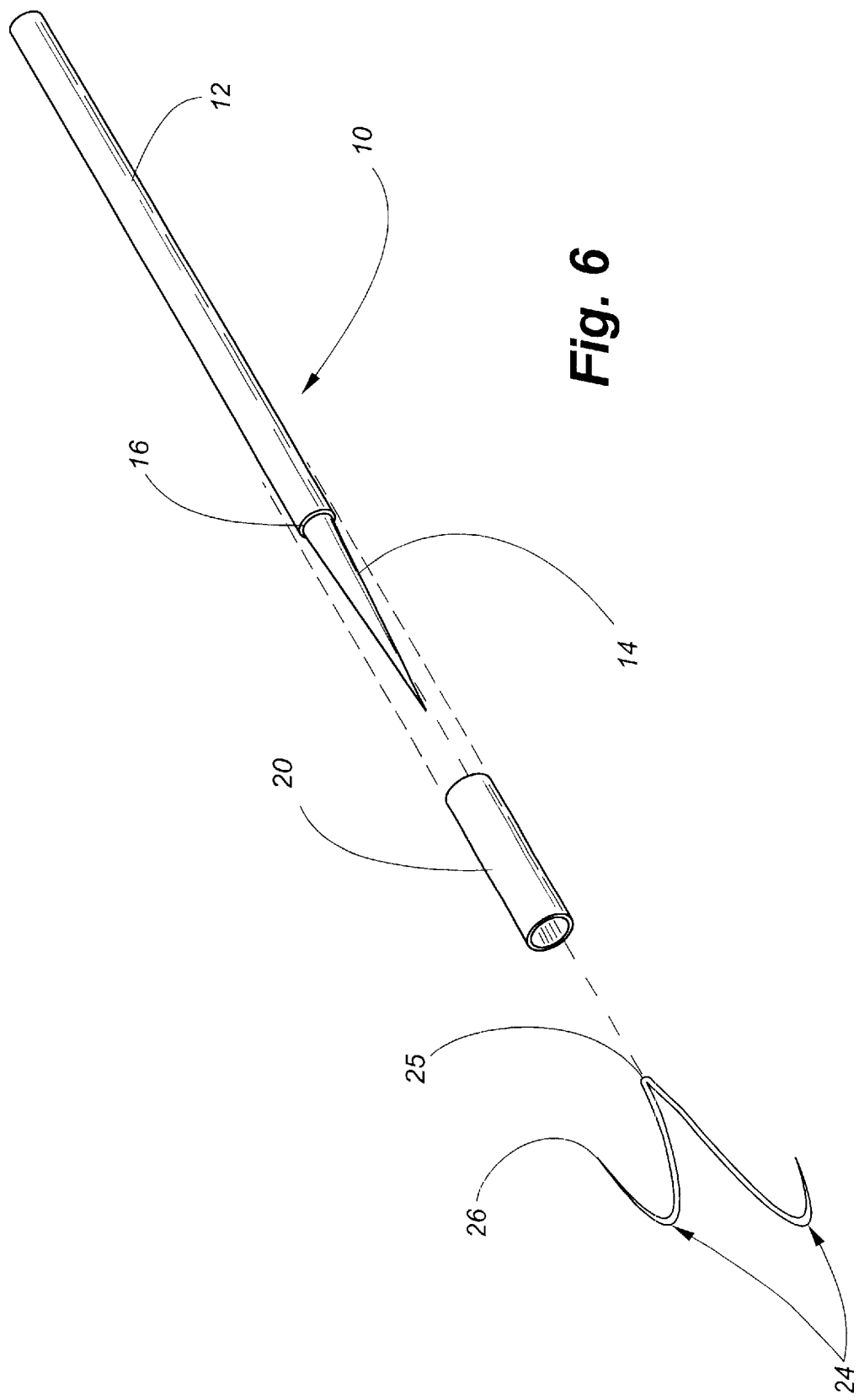
FIG. 6 is an exploded perspective view of the tissue localization device of FIG. 4.

Referring now to FIG. 2, a strain relief tube 20 of stainless steel or other suitable material has an inner diameter of 0.041 inches (1.04 mm) and is approximately 0.4 inches (~10 mm) long. The strain relief tube 20 fits over the forward end of the optical fiber 12, as shown in FIGS. 4–6, and straddles the junction 16 between the fiber and the conical tip 14. In the disclosed embodiment approximately 0.2 inches (5 mm) of the conical tip 14 is exposed beyond the forward end of the strain relief tube 20.

Figure 3:
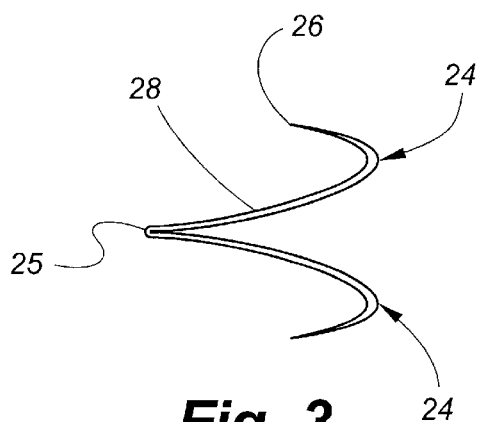
FIG. 3 is a side view of a pair of hook members of the tissue localization device of the disclosed embodiment.

Referring to FIG. 3, the tissue localization device 10 further comprises a pair of hook members 24 comprised of a flexible, resilient material such as 302 stainless steel. In the disclosed embodiment the two hook members 24 are formed from a single piece of wire and are thus joined at their rearward ends 25. Each hook member 24 comprises a barb 26 and a shank 28. To enable the hook members 24 to be temporarily straightened and to return to their original configurations without being permanently deformed, the device 10 is preferably heat-treated at temperatures of approximately 500° C. (932° F.) such that material hardening takes place.

As can be seen in FIGS. 4–6, the hook members 24 are mounted to the forward end of the device 10. More specifically, the rearward ends 25 of the hook members 24 are inserted into the forward end of the strain relief tube 20 and are advanced until they are wedged between the strain relief tube 20 and the conical tip 14 of the optical fiber 12. In this position the hook members 24 are disposed on opposite sides of the device 10 with the barbs 26 projecting outward and rearward. A suitable medical grade adhesive, such as LOCTITE 4014 Medical Device Instant Adhesive from Loctite Corporation, Hartford, Conn., is used to bond the hooks 24, the strain relief tube 20, and the conical tip 14 together.

Figure 7:
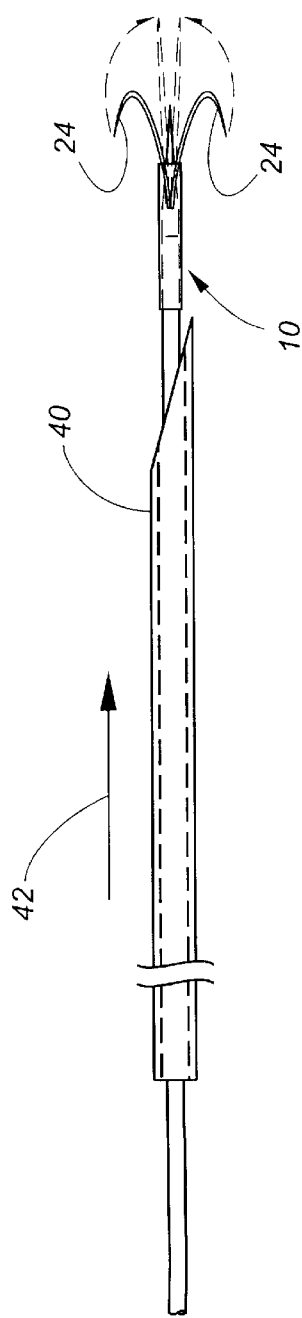
FIG. 7 is a side view showing the loading of the tissue localization device of FIG. 4 into a hollow cannula.

Referring now to FIG. 7, the device 10 is loaded into a hollow cannula 40 by inserting the rearward end of the optical fiber 12 into the forward end of the cannula 40 and advancing the cannula over the length of the optical fiber in the direction indicated by the arrow 42. As the cannula 40 confronts the hook members 24, the hook members are bent forward and inward until the hook members reside within the forward end of the cannula. Preferably this loading of the device 10 into the cannula 40 occurs prior to packaging and shipping the device so that the physician is spared the step of assembling the two components.

Figure 8:
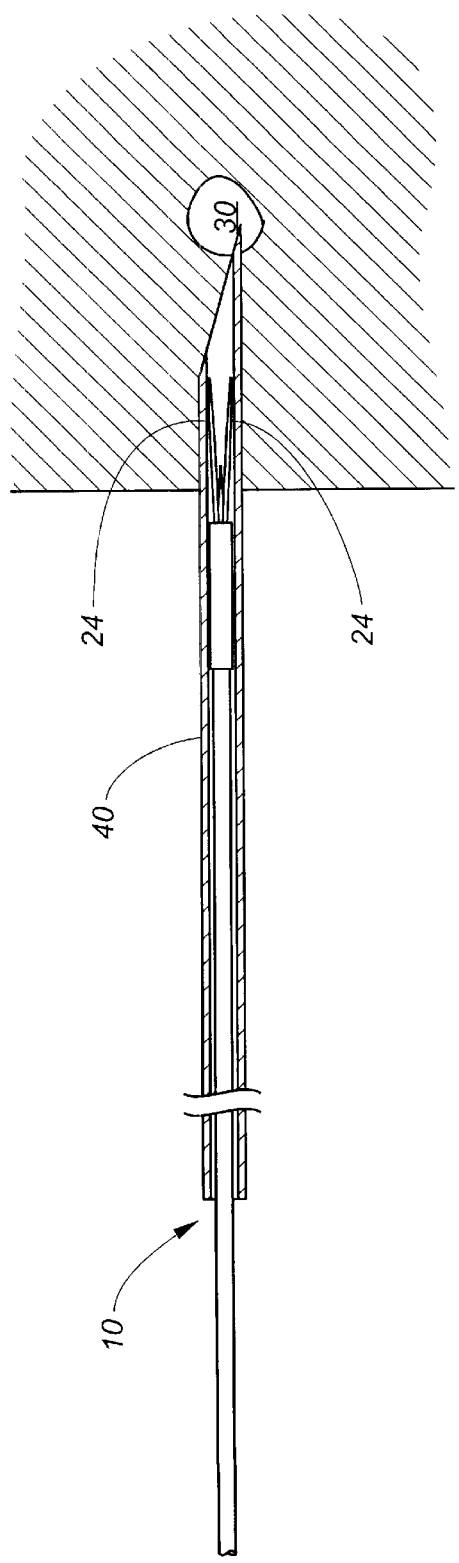
FIGS. 8–10 depict the use of the tissue localization device and cannula assembly of FIG. 7 to mark a suspicious lesion, where.
Figure 9:
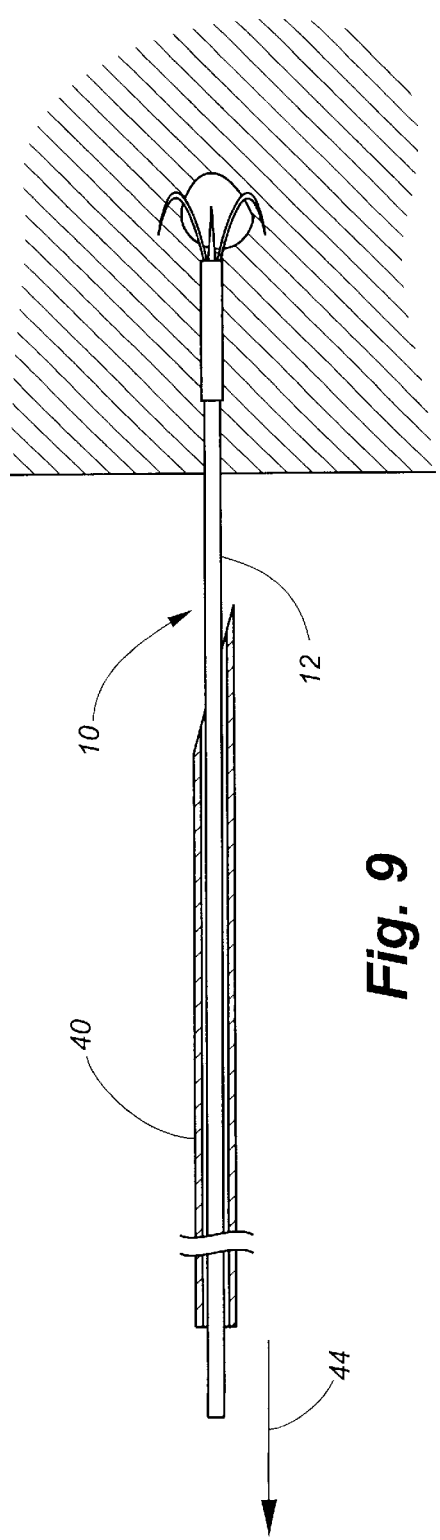

Operation of the device 10 will now be explained with reference to FIGS. 8–10. When a suspicious lesion 30 (the "target tissue") is located by a medical imaging modality such as ultrasound, mammography, magnetic resonance imaging, CT scan, or the like, the physician inserts the forward end of the cannula 40 into the patient and advances it to a location immediately adjacent the target tissue 30, as shown in FIG. 8. Location of the forward end of the cannula 40 may then be verified by a second imaging procedure.

When proper location of the forward end of the cannula 40 with respect to the lesion 30 has been verified, the cannula is withdrawn over the optical fiber 12 in the direction indicated by the arrow 44. As the cannula is withdrawn to expose the hook members 24, the hook members spring outward, as shown in FIG. 9, and the barbs 26 of the hook members anchor the conical tip 14 of the device 10 within the target tissue 30.

Should it become necessary to reposition the tip 14 of the device, the cannula 40 can be advanced over the optical fiber 12 in substantially the same manner explained above with reference to FIG. 7 to retract the hook members 24. Once the hook members 24 have been retracted within the forward end of the cannula 40, the cannula can be repositioned as needed, at which point the cannula is again withdrawn over the optical fiber 12 to deploy the hook members.

Figure 10:
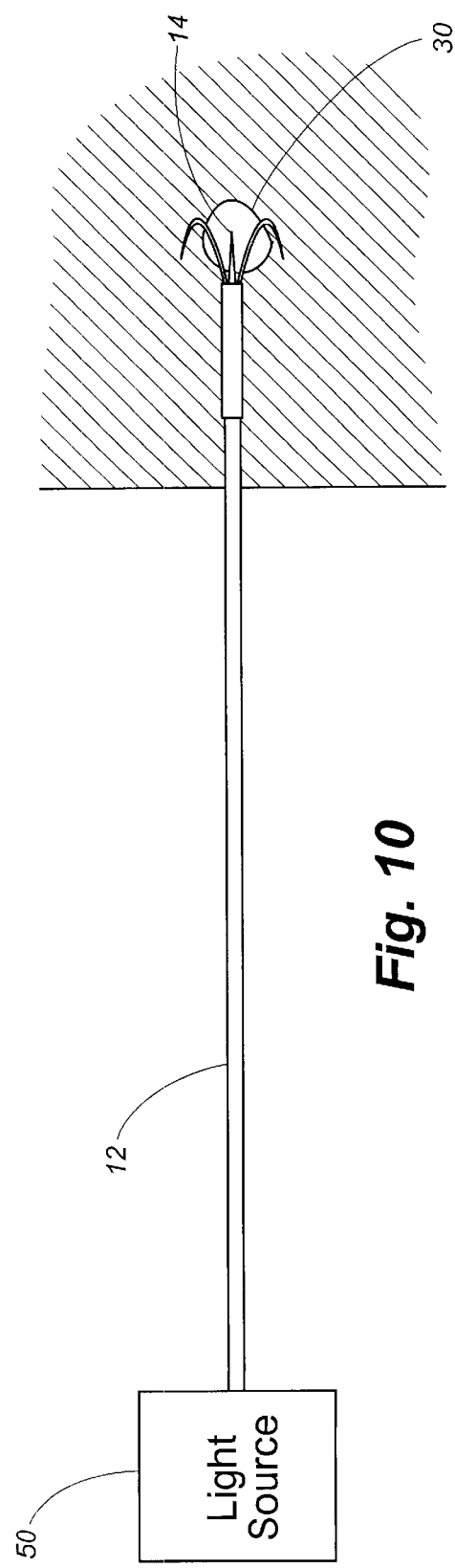

After the cannula 40 has been withdrawn over the rearward end of the optical fiber 12, the fiber is optically coupled to a light source 50, as shown schematically in FIG. 10. In the disclosed embodiment the light source 50 is a 5 mW, 635 nm wavelength laser, Class 3A, available from C.R. Bard, Inc. A beam of light is transmitted from the light source 50 down the optical fiber 12 and strikes the tip 14, where the matte external surface of the tip disperses the light. The physician can now easily see the tip 14 through several centimeters of tissue, facilitating location of the target tissue.

As can be seen from the foregoing explanation of the operation of the tissue localization device 10, the cannula 40 must be withdrawn over the rearward end of the optical fiber 12 prior to the fiber being coupled to the light source 50. However, it is also necessary to provide the rearward end of the optical fiber 12 with a means by which to couple the fiber to the light source 50. Since such couplings are conventionally integral with the fiber, these needs are in conflict. To meet these needs, the optical fiber 12 of the disclosed embodiment is coupled to the light source 50, both optically and physically, by means of a quick-connect coupling which can quickly, easily, and reliably be attached to the rearward end of the optical fiber 12 after the cannula 40 has been withdrawn.

Figure 11:
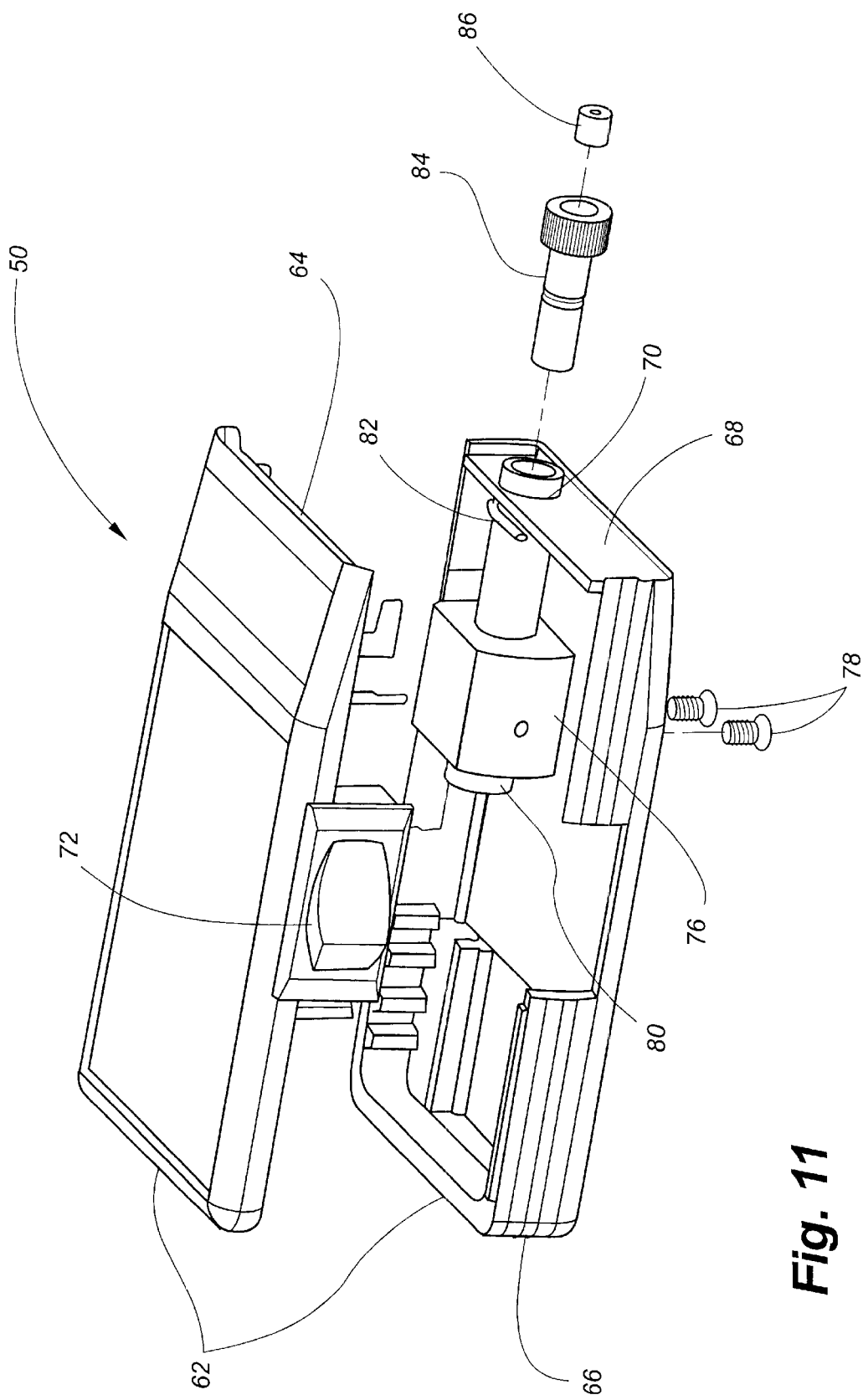
FIG. 11 is an exploded perspective view of the light source which is depicted schematically in FIG. 10.

FIG. 11 is an exploded view of the light source 50, heretofore shown only schematically. The light source 50 includes an enclosure 62, which is an off-the-shelf product (SERPAC Enclosure M6, Serpac, Inc.) with certain modifications, as will be explained below. The enclosure 62 includes an upper housing 64, a lower housing 66, and a front panel 68. The lower housing 66 includes recesses and electrical contacts (not shown) for a pair of "AA" batteries (also not shown), which power a laser, as will be explained.

The enclosure 62 is modified from its off-the-shelf configuration in the following respects. A circular hole 70 is formed in the front panel 68. The upper and lower housings 64, 66 are modified to accept a conventional rocker-type electrical switch 72, which is operable to open or close the electrical circuit powered by the batteries.

Referring further to FIG. 11, the light source 50 further includes a quick-release coupling comprising a mount 76 anchored to the lower housing 66 by means of screws 78. A laser 80, such as Part No. M635-5 from NVG, Inc., Hazelhurst, Ga., is attached to the rearward end of the mount 76. The laser 80 is operatively connected to the electrical circuit powered by the batteries and controlled by the electrical switch 72 so as to illuminate when the switch is activated.

A retainer clip 82 snaps onto the mount 76. An adapter 84 fits into the forward end of the mount 76. A rubber bushing 86 fits into the forward end of the adapter 84. Together, the mount 76, retainer clip 82, adapter 84, and bushing 86 comprise a quick-connect coupling device. Each of these components will be described below in more detail with reference to other drawing figures.

Figure 15:
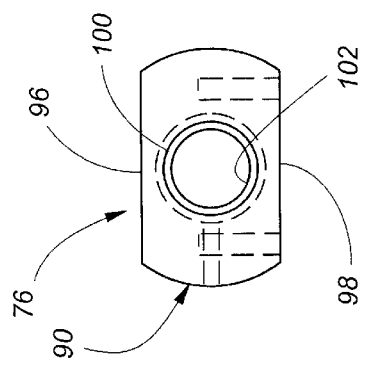
FIG. 15 is a front view of the mount of FIG. 12.

The mount 76 is shown in more detail in FIGS. 12–15. The mount 76 includes a body 90 having a front face 92 and a rear face 94. As can be seen in FIG. 15, the body 90 is shaped like a cylinder with flat upper and lower faces 96, 98.

The mount 76 further includes a tubular barrel 100 extending forward from the front face 92 of the body 90. A longitudinal through bore 102 extends through the barrel 100 and the body 90. A counterbore 104 having a diameter slightly larger than the through bore 102 is formed in the rear face 94 of the body 90 coaxial with the through bore. More specifically, the counterbore 104 is dimensioned to receive the forward end of the laser 80. Slots 105 are formed through the upper and lower walls of the barrel 100 of the mount 76.

Two vertical threaded bores 106 are formed in the lower face 98 of the body 90 of the mount 76, one on either side of the counterbore 104, to receive the mounting screws 78 (FIG. 1) for anchoring the mount 76 to the lower housing 66. A horizontal threaded bore 108 extends through a side wall of the body 90 and communicates with the counterbore 104.

Figure 16:
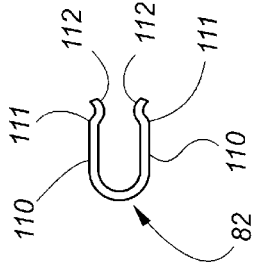
FIG. 16 is a top view of a retainer clip which snaps onto the mount of FIG. 12.
Figure 12:
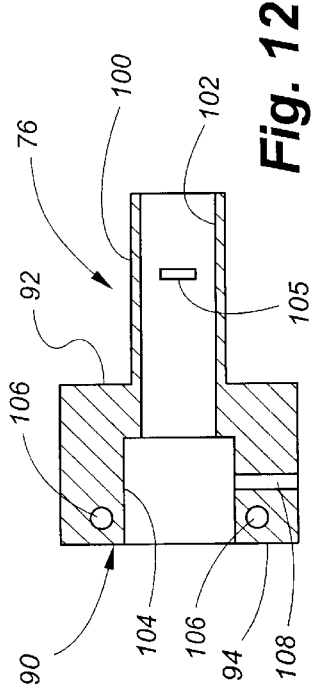
FIG. 12 is a top cutaway view of a mount of the light source of FIG. 11.
Figure 13:
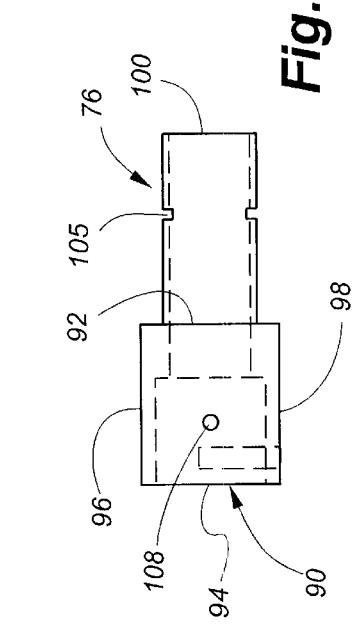
FIG. 13 is a side view of the mount of FIG. 12.
Figure 14:
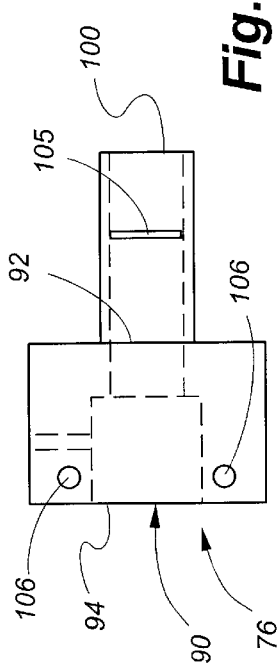
FIG. 14 is a bottom view of the mount of FIG. 12.

FIG. 16 illustrates the retainer clip 82. The retainer clip 82 is formed of a resilient material such as steel or nylon and includes a pair of arms 110. The arms 110 bend inward at a point 111 adjacent their free ends and then turn outward again, forming a pair of angled cam surfaces 112 which tend to bias the arms outward when the cam surfaces confront an object.

Referring now to FIGS. 17–19, the adapter 84 includes a generally cylindrical elongated body portion 120 having an enlarged cylindrical boss 122 at one end. The opposite end of the body portion 120 has a chamfered lead-in 123. The peripheral surface of the boss 122 is knurled to facilitate gripping. The exterior surface of the elongated cylindrical body portion 120 has a V-shaped notch 124 to extending around the periphery of the cylindrical body portion at an intermediate location. The outer diameter of the elongated cylindrical body portion 120 is dimensioned to fit snugly within the through bore 102 in the barrel 100 of the mount 76. The boss 122 at the forward end of the cylindrical body portion 120 has a larger diameter than the through bore 102 of the mount 76 and thus serves as a stop to limit the depth to which the adapter 84 can be inserted into the mount.

With particular reference now to FIG. 19, a longitudinal passageway 126 extends the length the cylindrical body portion 120 of the adapter 84. An enlarged counterbore 128 is formed in the forward end 130 of the adapter 84 coaxial with the passageway 126. At the rearmost end of the passageway 126, an annular stop 132 is formed. A small aperture 134 is provided in the central portion of the annular stop 132. The diameter of the passageway 126 is such as will receive the rearward end of the optical fiber 12 of the tissue localization device 10 therewithin. The aperture 134 of the annular stop 132 has a smaller diameter than the optical fiber 12, thus preventing the fiber from exiting the rearward end of the adapter 84.

Referring now to FIGS. 20 and 21, the cylindrical rubber bushing 86 includes a longitudinal passageway 140 having a diameter slightly smaller than the outer diameter of the optical fiber 12. The outer diameter of the bushing 86 is dimensioned to be received snugly within the counterbore 128 in the forward end of the adapter 84. The forward end of the passageway 140 flares outward to facilitate insertion of the rearward end of the optical fiber 12.

Figure 22:
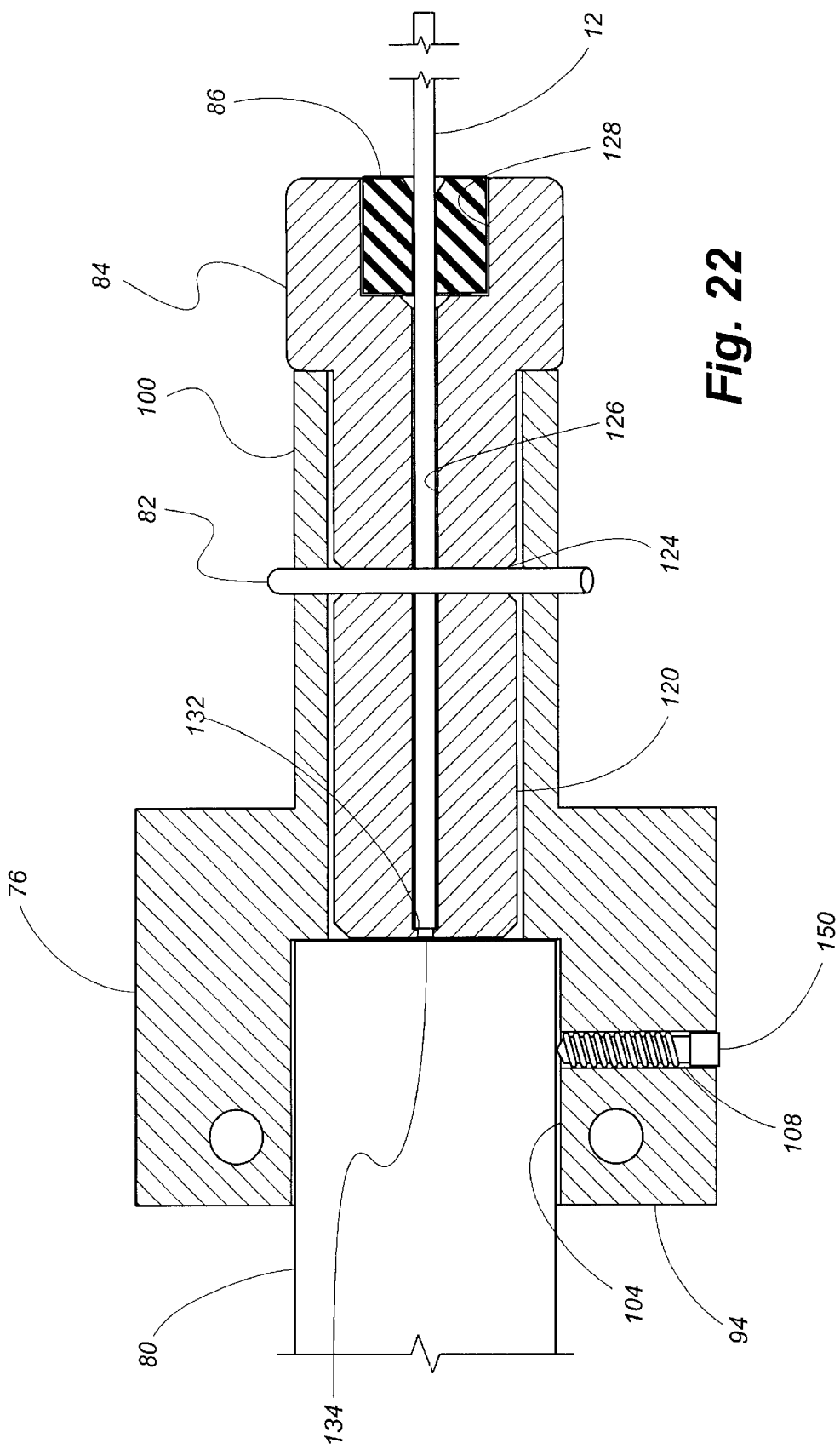
FIG. 22 is a top cutaway view of a laser, the adapter of FIG. 17, the bushing of FIG. 20, and the optical fiber of the tissue localization device of FIG. 4, all mounted to the mount of FIG. 12.

FIG. 22 shows the optical fiber 12 mounted to the adapter 84, with the adapter and the laser 80 assembled onto the mount 76. The cylindrical bushing 86 is fitted within the counterbore 128 in the forward end of the adapter 84. The rearward end of the optical fiber 12 is inserted through the rubber bushing 86 and through the longitudinal passageway 126 of the adapter 84 until it confronts the annular stop 132 at the rearward end of the adapter. The friction fit of the rubber bushing 86 around the periphery of the optical fiber 12 retains the optical fiber securely within the adapter 84. The rubber bushing 86 thus acts as a retention means for the optical fiber 12.

The cylindrical body portion 120 of the adapter 84 is inserted into the forward end of the barrel 100 of the mount 76. The retainer clip 82 is inserted over the barrel 100 of the mount 76 such that the arms 110 of the clip 82 protrude through the slots 105. The cam surfaces 112 anchor the clip 82 to the barrel 100. The cylindrical body portion 120 of the adapter 84 is inserted into the forward end of the barrel 100 until the arms 110 of the clip 82 engage the V-shaped notch 124 in the periphery of the adapter 84, locking the cylindrical body portion 120 in place. The boss 122 at the forward end of the cylindrical body portion 120 serves as a stop to limit the depth to which the adapter 84 can be inserted into the mount 76.

The forward (light emitting) end of the laser 80 is inserted into the counterbore 104 in the rearward face 94 of the mount 76 and advanced until the forward end of the laser rests on the base of the counterbore. A set screw 150 is threaded through the horizontal threaded bore 108 in the mount 76, the tip of the set screw clamping the laser 80 within the counterbore 104.

With the device thus assembled, the rearward end of the optical fiber 12 is disposed in the focal plane of the laser 80. When the laser 80 is activated, the beam of light shines through the aperture 134 in the annular stop 132 at the rearward end of the adapter 84 and strikes the rearward end of the optical fiber 12. The light is then transmitted up the optical fiber 12 to the tip 14 (FIGS. 1 and 4–6), which illuminates to enable the surgeon to locate the tip of the tissue localization device 10, as hereinabove explained.

The coupling of the disclosed embodiment provides a number of advantages. It can quickly, easily, and reliably be mounted to the rearward end of an optical fiber in an operating room environment. The rubber bushing 86 grips the fiber 12 and couples it to the light source 50 without the need for a separate mounting apparatus and without the need for tools. Because the coupling places the rearward end of the optical fiber 12 at a predetermined focal point, no additional optics are needed. Consequently the coupling is inexpensive to manufacture, thus lending itself to single-patient use.

As will be appreciated, the adapter 84 of the embodiment disclosed above provides certain advantages. As the cannula 40 is withdrawn over the length of the optical fiber 12, the entire length of the optical fiber is potentially contaminated. The light source 50 cannot easily be sterilized. Consequently if the contaminated end of the optical fiber 12 is coupled directly to the light source 50, contamination of the light source becomes a problem. By providing the adapter 84 to sheath the potentially contaminated end of the optical fiber 12, the potential for contamination of the light source 50 is minimized. Since the adapter 84 is inexpensive, it can simply be discarded along with the rest of the tissue localization device 10.

FIGS. 23–30 illustrate alternate means for retaining the rearward end of the optical fiber 12, once inserted into the coupling. More specifically, each of the designs now to be described constitutes an optical fiber retention means that can be substituted in place of the rubber bushing 86 of the embodiments previously described.

Figure 23:
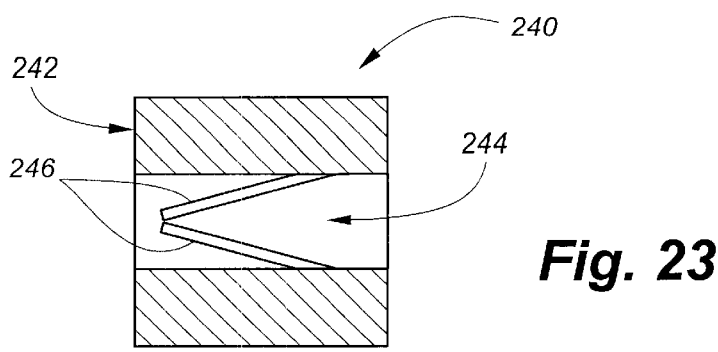
FIG. 23 is a side cutaway view of a first alternate embodiment of an optical fiber retention means for use with the mount of FIG. 12.
Figure 24:
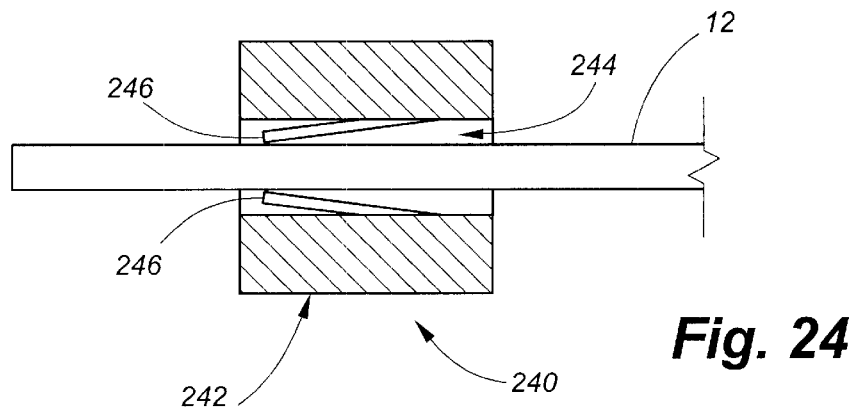
FIG. 24 is a side cutaway view of the optical fiber retention means of FIG. 23, showing the optical fiber secured therewithin.

FIGS. 23 and 24 depict an embodiment 240 which employs a duck-bill arrangement, wherein a housing 242 has a central bore 244. A pair of duck-bill members 246 are disposed within the bore 244. The members 246 are angled rearward, such that insertion of the end of the optical fiber 12 as shown in FIG. 24 biases the members apart. If a force is exerted which tends to extract the optical fiber 12 from the housing 242, the members 246 grip the fiber, preventing its withdrawal.

Figure 25:
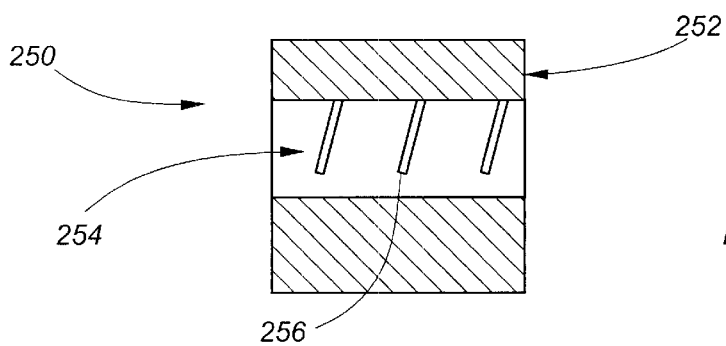
FIG. 25 is a side cutaway view of a second alternate embodiment of an optical fiber retention means for use with the mount of FIG. 12.
Figure 26:
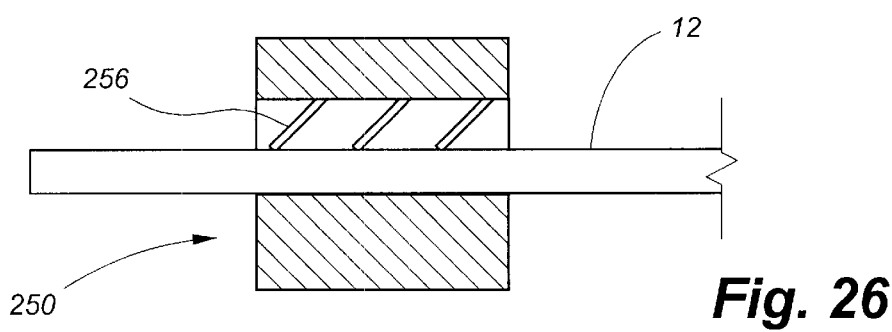
FIG. 26 is a side cutaway view of the optical fiber retention means of FIG. 25, showing the optical fiber secured therewithin.

FIGS. 25 and 26 illustrate an embodiment 250 which utilizes yet another arrangement to retain the end of the optical fiber 12. A housing 252 has a longitudinal bore 254. A plurality of teeth 256 extend downward from the upper wall of the bore 254 and are angled rearward. Insertion of the end of the optical fiber 12, as shown in FIG. 26, causes the teeth 256 to deflect rearward, permitting the fiber to pass beneath the teeth. The teeth 256 clamp the optical fiber against the bottom wall 258 of the bore 254. If a force is exerted which tends to extract the optical fiber 12 from the housing 252, the teeth 256 bite into the fiber, preventing its withdrawal.

Figure 27:
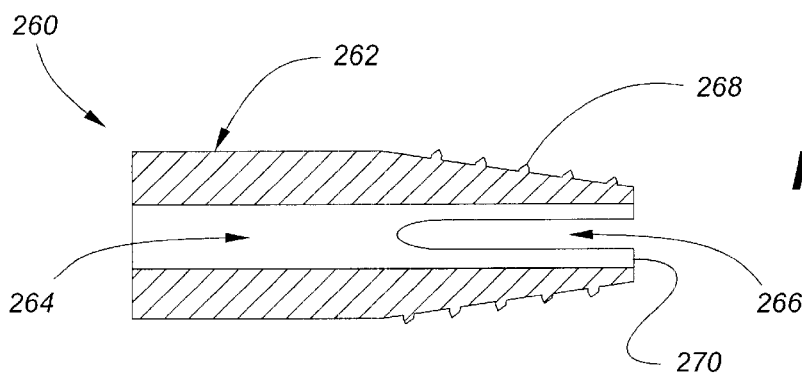
FIG. 27 is a side cutaway view of a third alternate embodiment of an optical fiber retention means for use with the mount of FIG. 12.
Figure 28:
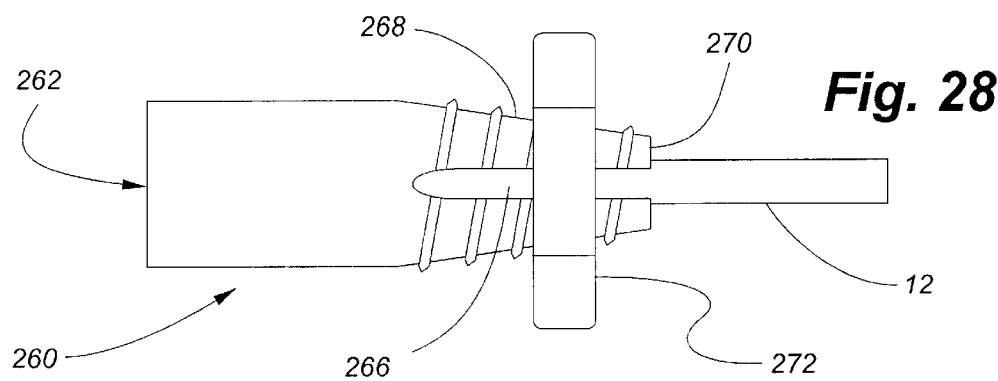
FIG. 28 is a side view of the optical fiber retention means of FIG. 27, showing the optical fiber secured therewithin.

FIGS. 27 and 28 show another embodiment 260 which employs a collet to retain the end of the optical fiber. A housing 262 includes a central bore 264, slots 266 in the walls of the housing, and an externally threaded housing surface 268. The housing 262 tapers gradually outward from its forward end 270. A nut 272 is threaded onto the end of the externally threaded housing surface 268. When the end of the optical fiber 12 is inserted into the bore 264 of the housing 262 and the nut 272 is tightened, the forward portion of the housing is compressed, clamping the fiber 12.

Figure 29:
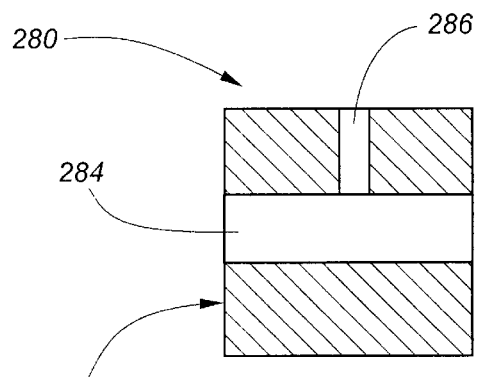
FIG. 29 is a side cutaway view of a fourth alternate embodiment of an optical fiber retention means for use with the mount of FIG. 12.
Figure 30:
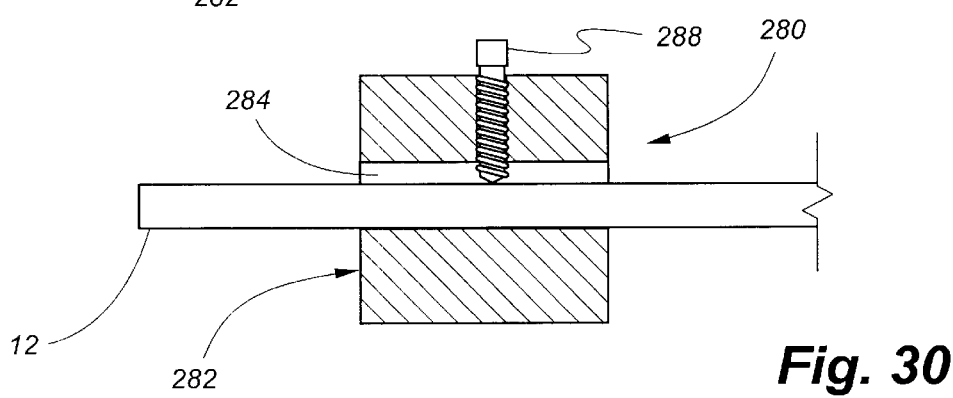
FIG. 30 is a side cutaway view of the optical fiber retention means of FIG. 29, showing the optical fiber secured therewithin.

FIGS. 29 and 30 show still another embodiment 280 of an optical fiber retention means. A housing 282 includes a central bore 284. A vertical threaded bore 286 extends from the upper surface of the housing and into the central bore 284. A screw 288 is threaded into the vertical bore 286. As shown in FIG. 32, when the optical fiber is inserted into the central bore 284 of the housing 282 and the screw 288 is tightened, the tip of the screw clamps the fiber against the opposite wall of the bore.

In addition to the optical fiber retention means hereinabove described, other means of securing an optical fiber to a mount can be used, including adhesives.

Finally, it will be understood that the preferred embodiment has been disclosed by way of example, and that other modifications may occur to those skilled in the art without departing from the scope and spirit of the appended claims.

What is claimed is:

1. An apparatus for marking a location within the tissue of a patient, comprising:

an optical fiber having a forward end, a rearward end, and an outer diameter, said forward end of said optical fiber being shaped into a tapered tip beginning at a transition point along the length of said optical fiber;

anchor means operatively associated with a forward portion of said optical fiber for engaging the tissue of a patient to secure said tip of said optical fiber within the tissue of said patient;

a light source;

a mount to which said light source is mounted; and coupling means operative upon insertion of said rearward end of said optical fiber into said coupling means for gripping said optical fiber for coupling said rearward end of said optical fiber to said mount so as to optically couple said light source to said optical fiber while physically isolating said optical fiber from said light source.

2. The apparatus of claim 1, wherein said coupling means substantially encapsulates said rearward end of said optical fiber so as to prevent any contamination on said rearward end of said optical fiber from contacting said mount.

3. The apparatus of claim 1, wherein said light source has a focal plane, and wherein said coupling means further comprises means for positioning said rearward end of said optical fiber in said focal plane of said light source.

4. The apparatus of claim 1, wherein said rearward end of said optical fiber is coupled to said coupling means by a friction fit between said coupling means and said rearward end of said optical fiber.

5. The apparatus of claim 4, wherein said coupling means comprises a rubber bushing having a passageway through which said rearward end of said optical fiber is inserted, said passageway being dimensioned to receive said rearward end of said optical fiber in a friction fit.

6. The apparatus of claim 4, wherein said coupling means comprises a pair of mutually opposed, angled tab members arranged in duck-bill fashion, and wherein said friction fit between said coupling means and said rearward end of said optical fiber comprises a friction fit between said duck-bill tab members and said rearward end of said optical fiber.

7. The apparatus of claim 4, wherein said coupling means comprises a plurality of resilient angled teeth having free ends disposed adjacent a bearing surface, and wherein said friction fit between said coupling means and said rearward end of said optical fiber comprises said teeth biasing said rearward end of said optical fiber against said bearing surface.

8. The apparatus of claim 1, wherein said coupling means is coupled to said mount by a detent fit between said coupling means and said mount.

9. The apparatus of claim 8, wherein said mount comprises a cavity dimensioned to receive said coupling means therewithin in a detent fit, and wherein said coupling means is coupled to said mount by inserting said coupling means into said cavity of said mount.

10. A method for marking a location within the tissue of a patient, comprising the steps of:

inserting a hollow needle into the tissues of a patient so that a forward end of said hollow needle is positioned adjacent a target location;

inserting into a rearward end of said hollow needle an optical fiber having retention means located adjacent a forward end thereof;

advancing said optical fiber through said hollow needle until said retention means emerges from said forward end of said hollow needle and anchors said forward end of said optical fiber at said target location;

withdrawing said hollow needle over said optical fiber and off a rearward end thereof;

subsequent to said step of withdrawing said hollow needle, attaching an adapter to said rearward end of said optical fiber; and coupling said optical fiber to a light source by attaching said adapter to a mount to which said light source is mounted.

11. The method of claim 10, wherein said step of attaching an adapter to said rearward end of said optical fiber comprises the step of attaching said adapter to said rearward end of said optical fiber by way of a friction fit.

12. The method of claim 10, wherein said step of attaching said adapter to said mount comprises the step of attaching said adapter to said mount by way of a detent fit.

13. An apparatus for marking a location within the tissue of a patient and adapted for use with a mount and a light source mounted to said mount, said apparatus comprising:

an optical fiber having a forward end and a rearward end;

anchor means operatively associated with a forward portion of said optical fiber for engaging the tissue of a patient to secure said forward end of said optical fiber within the tissue, of said patient; and an adapter for engaging said rearward end of said optical fiber by way of a friction fit and for engaging said mount so as to optically couple said optical fiber to said light source while physically isolating said optical fiber from said mount.

14. The apparatus of claim 13, wherein said adapter substantially encapsulates said rearward end of said optical fiber so as to prevent said rearward end of said optical fiber from contacting said mount.

15. The apparatus of claim 13, wherein said adapter comprises a rubber bushing, said rubber bushing having a passageway through which said rearward end of said optical fiber is inserted, said passageway being dimensioned to receive said rearward end of said optical fiber in a friction fit.

16. An apparatus for marking a location within the tissue of a patient and adapted for use with a mount and a light source mounted to said mount, said apparatus comprising:

an optical fiber having a forward end and a rearward end;

anchor means operatively associated with a forward portion of said optical fiber for engaging the tissue of a patient to secure said forward end of said optical fiber within the tissue of said patient; and an adapter for engaging said rearward end of said optical fiber by way of a detent fit.

17. The apparatus of claim 15, wherein said adapter substantially encapsulates said rearward end of said optical fiber so as to prevent said rearward end of said optical fiber from contacting said mount.

18. An apparatus for marking a location within the tissue of a patient, comprising:

an optical fiber having a forward end, a rearward end, and an outer diameter, said forward end of said optical fiber being shaped into a tapered tip beginning at a transition point along the length of said optical fiber;

anchor means operatively associated with a forward portion of said optical fiber for engaging the tissue of a patient to secure said tip of said optical fiber within the tissue of said patient;

a light source;

a mount to which said light source is mounted; and coupling means for coupling said rearward end of said optical fiber to said mount so as to optically couple said light source to said optical fiber while physically isolating said optical fiber from said light source, said coupling means including a passage into which said rearward end of said optical fiber is inserted, and said coupling means further comprising clamping means operable to clamp said rearward end of said optical fiber within said passage.

19. The apparatus of claim 18, wherein said clamping means is operable to clamp said rearward end of said optical fiber within said passage without the use of a tool.

20. The apparatus of claim 18, wherein said coupling means comprises a collet, and wherein said clamping means comprises said collet frictionally engaging said rearward end of said optical fiber.

21. The apparatus of claim 18, wherein said coupling means comprises threaded retention means and a bearing surface, and wherein said friction fit between said coupling means and said rearward end of said optical fiber comprises said threaded retention means clamping said rearward end of said optical fiber against said bearing surface.

* * * * *